United States Patent [19]
Viola et al.

[11] Patent Number: 5,954,259
[45] Date of Patent: Sep. 21, 1999

[54] SELF-CONTAINED POWERED SURGICAL APPARATUS FOR APPLYING SURGICAL FASTENERS

[75] Inventors: Frank J. Viola, Sandy Hook; Daniel E. Alesi, Sherman; Dominick L. Mastri, Bridgeport; Wayne P. Young, Brewster; Richard N. Granger, Huntington; Kenneth E. Toso, Wilton, all of Conn.

[73] Assignee: United States Surgical Corporation, Norwalk, Conn.

[21] Appl. No.: 08/883,790

[22] Filed: Jun. 27, 1997

Related U.S. Application Data

[63] Continuation of application No. 08/319,852, Oct. 7, 1994, abandoned, which is a continuation-in-part of application No. 08/287,455, Aug. 5, 1994, abandoned.

[51] Int. Cl.⁶ .................................................. A61B 17/068
[52] U.S. Cl. .................... 227/176.1; 227/79; 227/178.1; 227/180.1
[58] Field of Search .............................. 227/176.1, 175.1, 227/178.1, 180.1, 19

[56] References Cited

U.S. PATENT DOCUMENTS

| | | |
|---|---|---|
| 1,881,250 | 10/1932 | Tomlinson . |
| 3,618,842 | 11/1971 | Bryan . |
| 3,815,476 | 6/1974 | Green et al. . |
| 3,952,748 | 4/1976 | Kaliher et al. . |
| 4,071,029 | 1/1978 | Richmond et al. . |
| 4,289,131 | 9/1981 | Mueller . |
| 4,334,539 | 6/1982 | Childs et al. . |
| 4,484,503 | 11/1984 | Sitte et al. . |
| 4,489,724 | 12/1984 | Arnegger . |
| 4,494,057 | 1/1985 | Hotta . |
| 4,520,817 | 6/1985 | Green . |
| 4,605,001 | 8/1986 | Rothfuss et al. . |
| 4,610,383 | 9/1986 | Rothfuss et al. . |
| 4,644,952 | 2/1987 | Patipa et al. . |
| 4,650,460 | 3/1987 | Roizenblatt . |
| 4,655,673 | 4/1987 | Hawkes . |
| 4,705,038 | 11/1987 | Sjostrom et al. . |
| 4,733,118 | 3/1988 | Mihalko . |
| 4,771,774 | 9/1988 | Simpson et al. . |
| 4,784,137 | 11/1988 | Kulik et al. . |
| 4,867,158 | 9/1989 | Sugg . |
| 4,887,599 | 12/1989 | Muller . |
| 4,936,845 | 6/1990 | Stevens . |
| 4,995,877 | 2/1991 | Ams et al. . |
| 5,040,715 | 8/1991 | Green et al. . |
| 5,059,203 | 10/1991 | Husted . |
| 5,071,430 | 12/1991 | de Salis et al. . |
| 5,133,359 | 7/1992 | Kedem . |

(List continued on next page.)

FOREIGN PATENT DOCUMENTS

| | | |
|---|---|---|
| 0156774 | 10/1985 | European Pat. Off. . |
| 0216532 | 4/1987 | European Pat. Off. . |
| 0536903 | 4/1993 | European Pat. Off. . |
| 0539762 | 5/1993 | European Pat. Off. . |
| 0552050 | 7/1993 | European Pat. Off. . |
| 0593920 | 4/1994 | European Pat. Off. . |
| 0598579 | 5/1994 | European Pat. Off. . |
| 0621006 | 10/1994 | European Pat. Off. . |
| 2660851 | 10/1991 | France . |
| 2903159 | 7/1980 | Germany . |
| 3114135 | 10/1982 | Germany . |
| 4213426 | 10/1992 | Germany . |
| 51-149985 | 5/1975 | Japan . |
| 659146 | 4/1979 | U.S.S.R. . |
| 9308754 | 5/1993 | WIPO . |
| 9314706 | 8/1993 | WIPO . |

*Primary Examiner*—Scott A. Smith

[57] ABSTRACT

A self-contained powered surgical apparatus for applying surgical fasteners to body tissue is disclosed which includes a handle assembly, a gear motor assembly disposed within the handle assembly, a power source disposed within the handle assembly for energizing the motor assembly, an elongated body extending distally from the handle assembly, a cartridge assembly detachably connected to a distal end portion of the elongated body, and an elongated drive shaft extending through the elongated body and detachably coupling the motor assembly to the cartridge assembly.

26 Claims, 9 Drawing Sheets

U.S. PATENT DOCUMENTS

| | | |
|---|---|---|
| 5,133,713 | 7/1992 | Huang et al. . |
| 5,133,729 | 7/1992 | Sjostrom . |
| 5,170,925 | 12/1992 | Madden et al. . |
| 5,192,292 | 3/1993 | Cezana et al. . |
| 5,201,750 | 4/1993 | Hocherl et al. . |
| 5,207,697 | 5/1993 | Carusillo et al. . |
| 5,221,279 | 6/1993 | Cook et al. . |
| 5,237,884 | 8/1993 | Seto . |
| 5,249,583 | 10/1993 | Mallaby . |
| 5,258,007 | 11/1993 | Spetzler et al. . |
| 5,261,877 | 11/1993 | Fine et al. . |
| 5,268,622 | 12/1993 | Philipp . |
| 5,289,963 | 3/1994 | McGarry et al. . |
| 5,312,023 | 5/1994 | Green et al. . |
| 5,318,221 | 6/1994 | Green et al. . |
| 5,326,013 | 7/1994 | Green et al. . |
| 5,403,327 | 4/1995 | Thornton et al. .......................... 227/91 |
| 5,433,721 | 7/1995 | Hooven et al. ............................ 227/19 |
| 5,467,911 | 11/1995 | Tsuruta et al. . |
| 5,482,197 | 1/1996 | Green et al. .............................. 227/19 |
| 5,485,947 | 1/1996 | Olson et al. .............................. 227/19 |

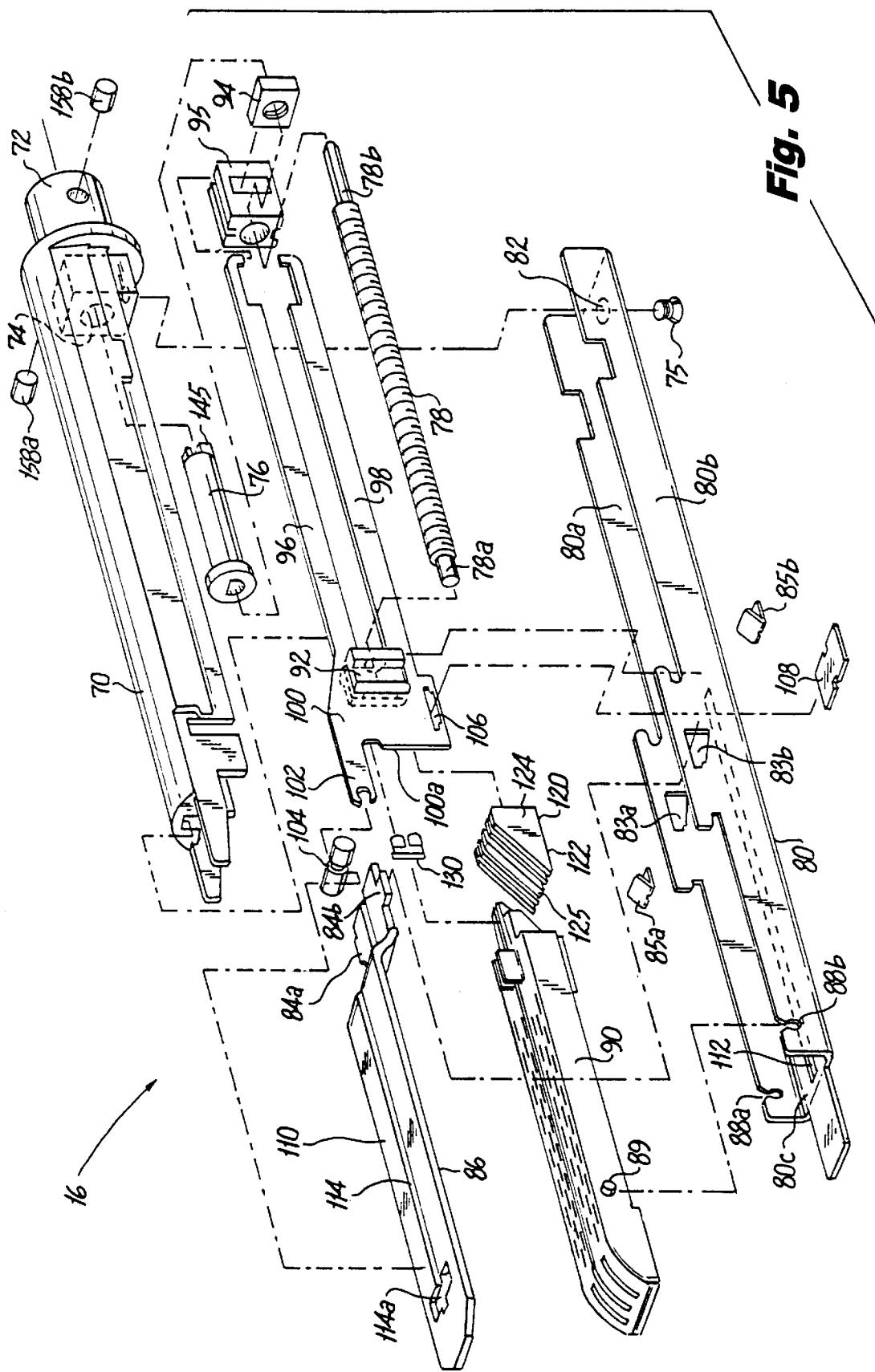

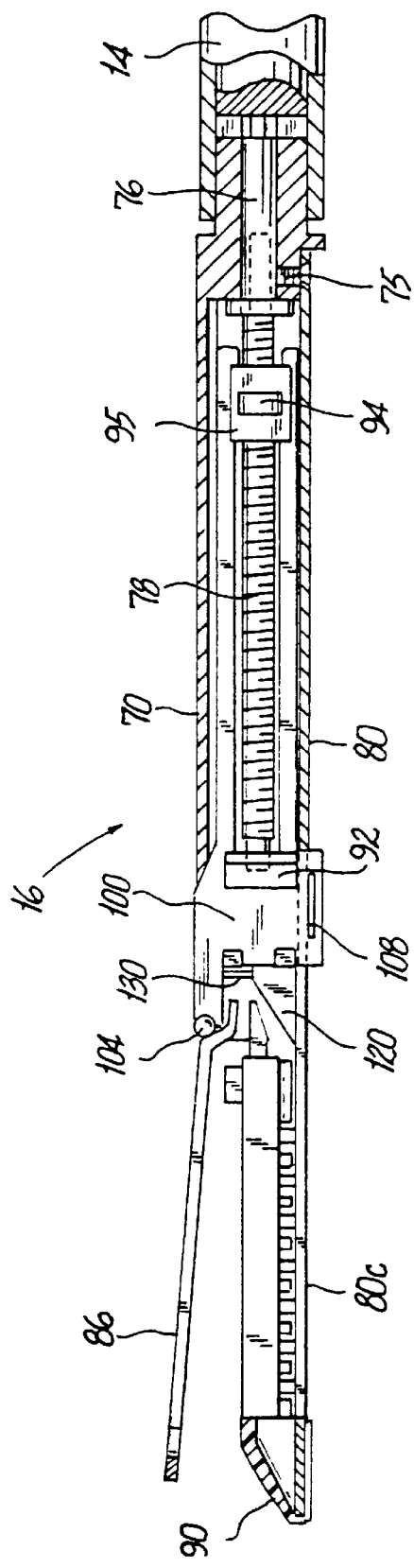
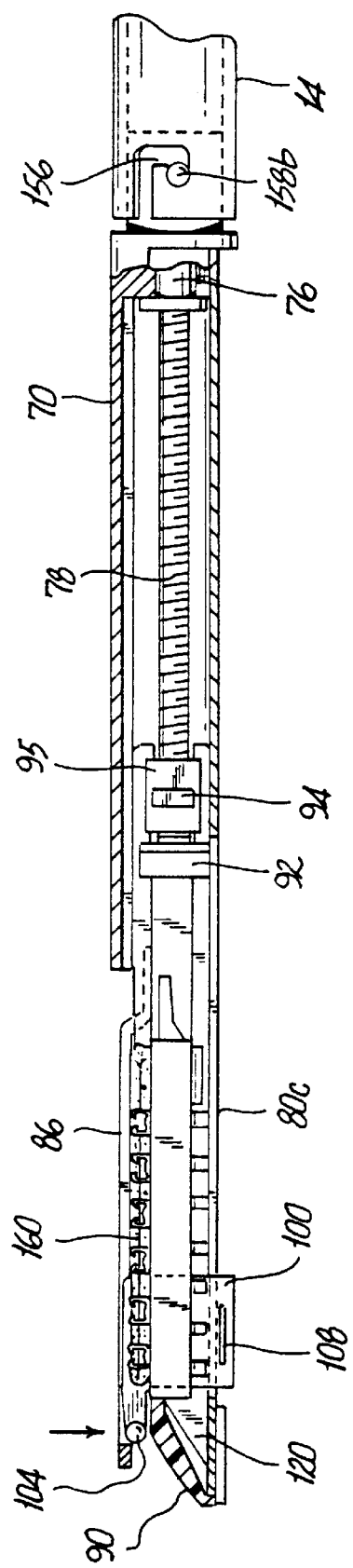
Fig. 9
Fig. 10

SELF-CONTAINED POWERED SURGICAL APPARATUS FOR APPLYING SURGICAL FASTENERS

CROSS REFERENCE TO RELATED APPLICATIONS

This is a continuation of application Ser. No. 08/319,852 filed on Oct. 7, 1994 abandoned, which is a continuation-in-part of application Ser. No. 08/287,455 filed Aug. 5, 1994 now abandoned, the contents of which are incorporated herein by reference.

BACKGROUND

1. Technical Field

This application relates to a surgical apparatus, and more particularly, to an apparatus for sequentially applying a plurality of surgical fasteners to body tissue and optionally incising the fastened tissue.

2. Background of Related Art

Surgical devices wherein tissue is first grasped or clamped between opposing jaw structure and then joined by means of surgical fasteners are well known in the art. In some instruments a knife is provided to cut the tissue which has been joined by the fasteners. The fasteners are typically in the form of surgical staples however, two part polymeric fasteners are also utilized.

Instruments for this purpose can comprise two elongated members which are respectively used to capture or clamp tissue. Typically, one of the members carries a disposable cartridge which houses a plurality of staples arranged in at least two lateral rows while the other member comprises an anvil which defines a surface for forming the staple legs as the fasteners are driven from the edge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut and/or open the stapled tissue between the rows of staples. Such instruments are disclosed in U.S. Pat. No. 3,079,606 to Bobrov, et al and U.S. Pat. No. 3,490,675 to Green.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through narrow a cannula inserted through small entrance wounds in the skin. In order to address the specific needs of endoscopic and/or laparoscopic surgical procedures, endoscopic surgical stapling devices have been developed and are disclosed in U.S. Pat. Nos. 5,040,715 and 5,318,221. In general, these instruments are provided with clamping structure to effect approximation of an anvil and a cartridge to secure tissue therebetween, and staple firing structure to effect sequential ejection of a plurality of fasteners from the cartridge after the tissue has been secured.

The instruments discussed above all require some degree of manually applied force in order to clamp, fasten and/or cut tissue. Surgeons have thus recognized the benefits of using self-powered instruments that are actuable with only a limited degree of physical force. Self-powered surgical instruments have been provided to serve these needs and include both gas powered surgical staplers, as shown, for example, in U.S. Pat. No. 5,312,023, and electrically powered surgical instruments as described in U.S. Pat. Nos. 4,365,638 and 5,258,007, and European Patent Application No. 0 552 050. In general, prior art electrically powered surgical instruments have been driven by external power sources. The instruments were connected to the power sources by conductive cables. Such cables could, however, become entangled during a surgical procedure, thereby complicating the operation. It would therefore be beneficial to provide a self-contained powered surgical apparatus for applying surgical fasteners to body tissue. It would also be beneficial if such self contained powered apparatus could be reloadable.

SUMMARY

The subject application is directed to a self-contained powered surgical apparatus for applying surgical fasteners to body tissue. The apparatus includes a handle assembly, a motor assembly disposed within the handle assembly, a power source disposed within the handle assembly for energizing the motor assembly, an elongated body extending distally from the handle assembly, and a cartridge assembly detachably connected to a distal end portion of the elongated body.

The cartridge assembly includes a housing supporting a plurality of surgical fasteners, an anvil associated with the housing and mounted for movement between an open position and a closed position, an actuation mechanism configured to translate relative to the housing and the anvil to progressively move the anvil from the open position to the closed position and to sequentially eject surgical fasteners from the housing to be formed against the anvil, and an axial drive screw threadably associated with the actuator for effectuating the longitudinal translation thereof. The powered surgical apparatus further includes an elongated drive shaft which extends through the elongated body and couples the motor assembly to the axial drive screw of the cartridge assembly.

Preferably, the handle assembly includes an elongate barrel portion within which the motor assembly is disposed, and a depending handle gripping portion within which the power source is disposed. A trigger mechanism is associated with the handle assembly for selectively actuating the motor assembly, and a switching mechanism is associated with the trigger mechanism for selectively reversing the polarity of the motor assembly.

Preferably, the elongated body and the cartridge assembly can rotate axially with respect to a longitudinal axis of the elongated body. Means are preferably provided for preventing such rotation comprising a plurality of recesses formed in and circumferentially disposed about a distal portion of the handle assembly, and an annular collar which is formed of a resilient material and mounted about a proximal end portion of the elongated body. The annular collar includes a pair of diametrically opposed radially inwardly extending protuberances which are dimensioned and configured to engage the circumferenfially disposed recesses. When the protuberances are engaged in respective recesses, rotation of the elongated body with respect to the handle assembly is prevented. Application of a radially inwardly directed force disengages the protuberences from the recesses to allow rotation.

Further features of the powered surgical apparatus of the subject application will become more readily apparent to those skilled in the art from the following detailed description of the apparatus taken in conjunction with the drawings.

BRIEF DESCRIPTION OF THE DRAWINGS

Various embodiments of the surgical apparatus of the subject application will be described hereinbelow with reference to the drawings wherein:

FIG. 5 is an exploded perspective view of the cartridge assembly of the powered surgical apparatus illustrated in FIG. 1;

FIG. 9 is a side elevational view in cross-section illustrating the cartridge assembly of the surgical apparatus of FIG. 1 prior to firing the fasteners;

FIG. 10 is a side elevational view in cross-section illustrating the cartridge assembly of the surgical apparatus of FIG. 1 subsequent to the fasteners being fired.

DETAILED DESCRIPTION OF PREFERRED EMBODIMENTS

Figure 1:
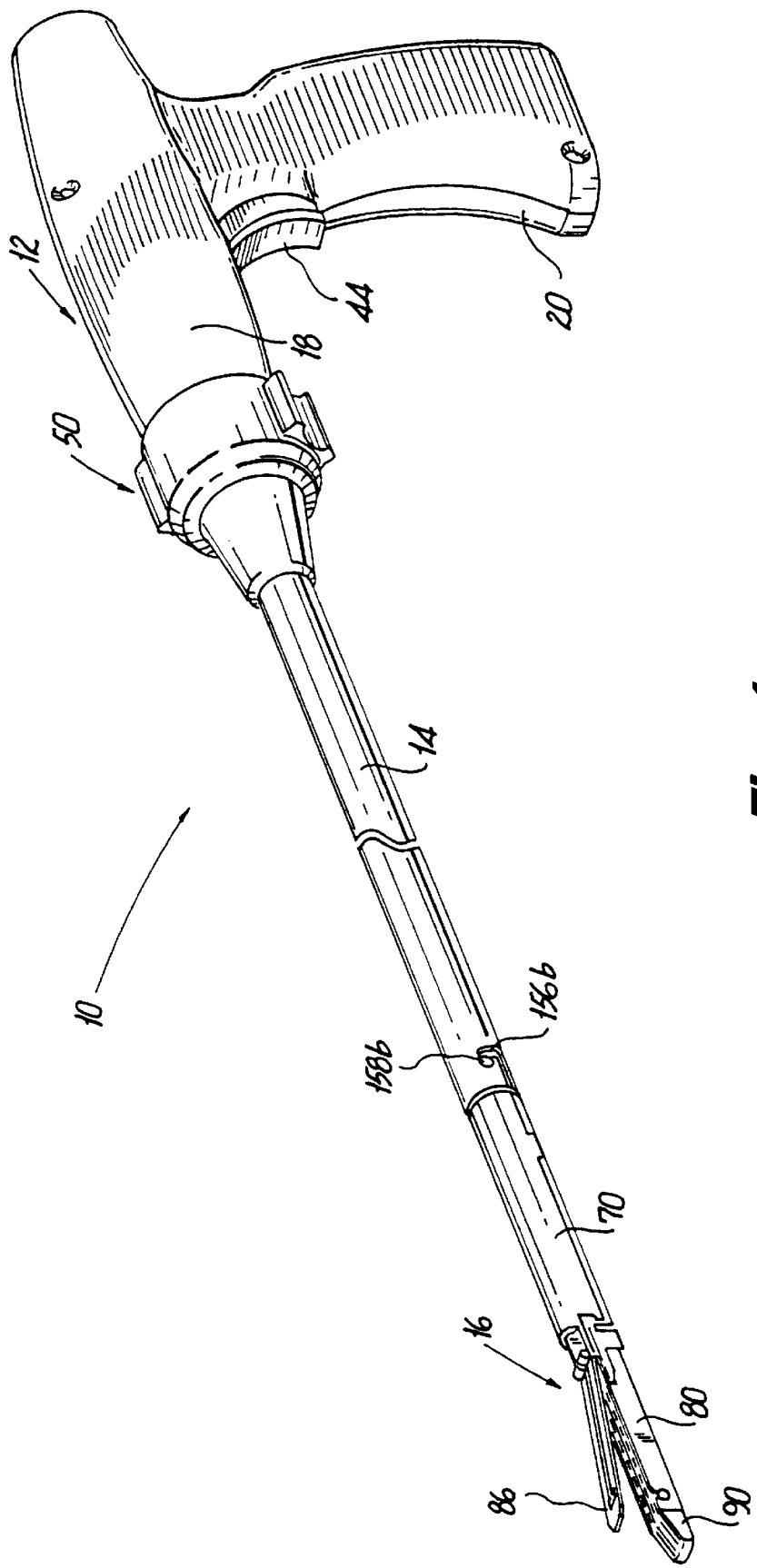
FIG. 1 is a perspective view of a powered surgical stapling apparatus constructed in accordance with a preferred embodiment.

In the drawings and in the description which follows, the term "proximal", as is traditional, will refer to the end of the apparatus which is closest to the operator, while the term "distal" will refer to the end of the apparatus which is furthest from the operator.

The present apparatus shall be discussed in terms of both endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to arthroscopic and/or laparoscopic procedures.

Referring now to the drawings wherein like reference numerals identify similar structural elements of the subject invention, there is illustrated in FIG. 1 a self-contained powered surgical stapler constructed in accordance with a preferred embodiment of the subject invention and designated generally by reference numeral 10. Surgical stapler 10 is configured to clamp body tissue, apply a plurality of surgical fasteners to the body tissue, and form an incision in the fastened body tissue during a laparoscopic surgical procedure. In brief, surgical stapler 10 includes a handle portion 12, an elongate body portion 14 extending distally from handle portion 12, and a cartridge assembly 16 detachably connected to a distal end of body portion 14.

Figure 2:
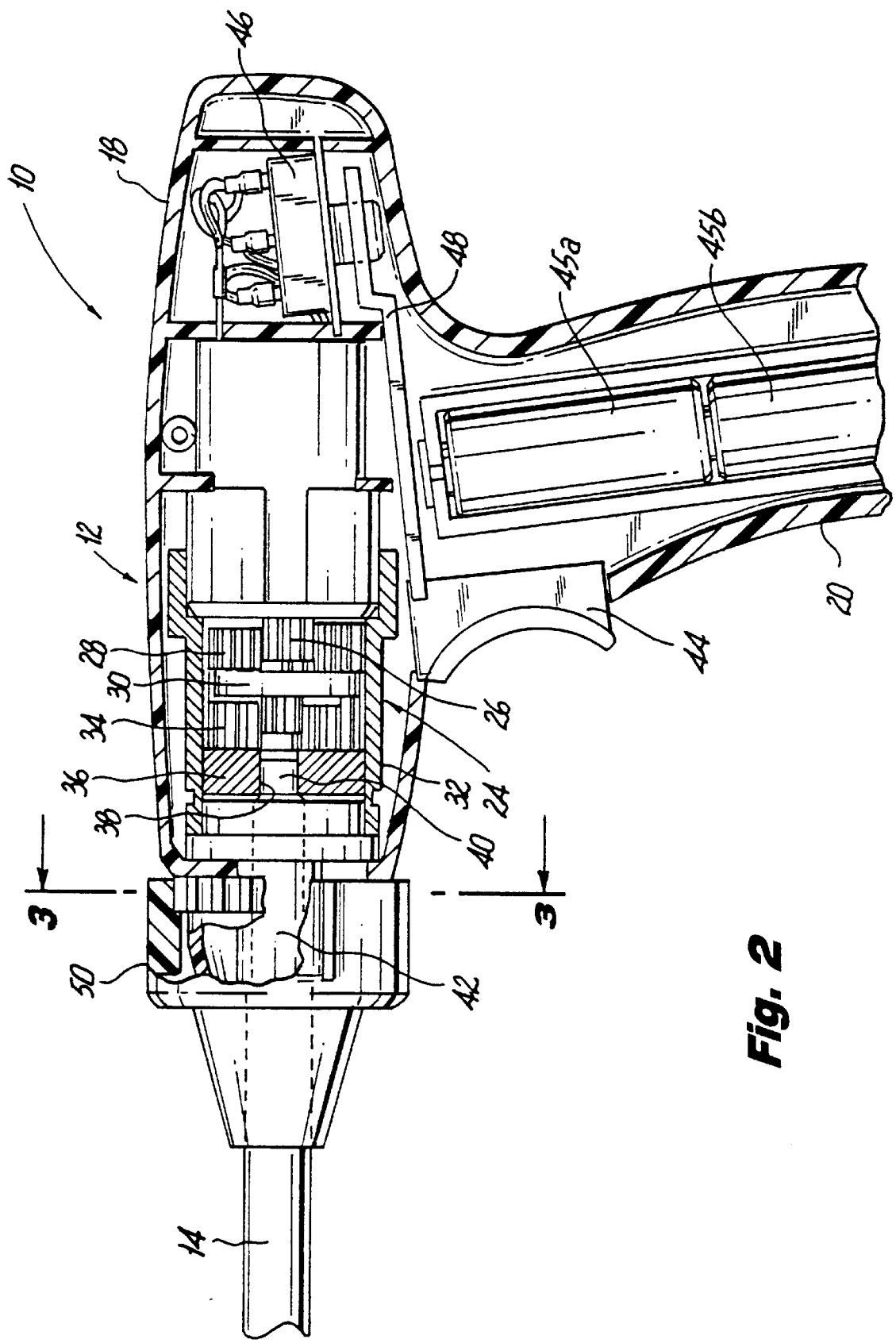
FIG. 2 is a side elevational view in cross-section of the handle assembly of the powered surgical stapling apparatus of FIG. 1.
Figure 2A:
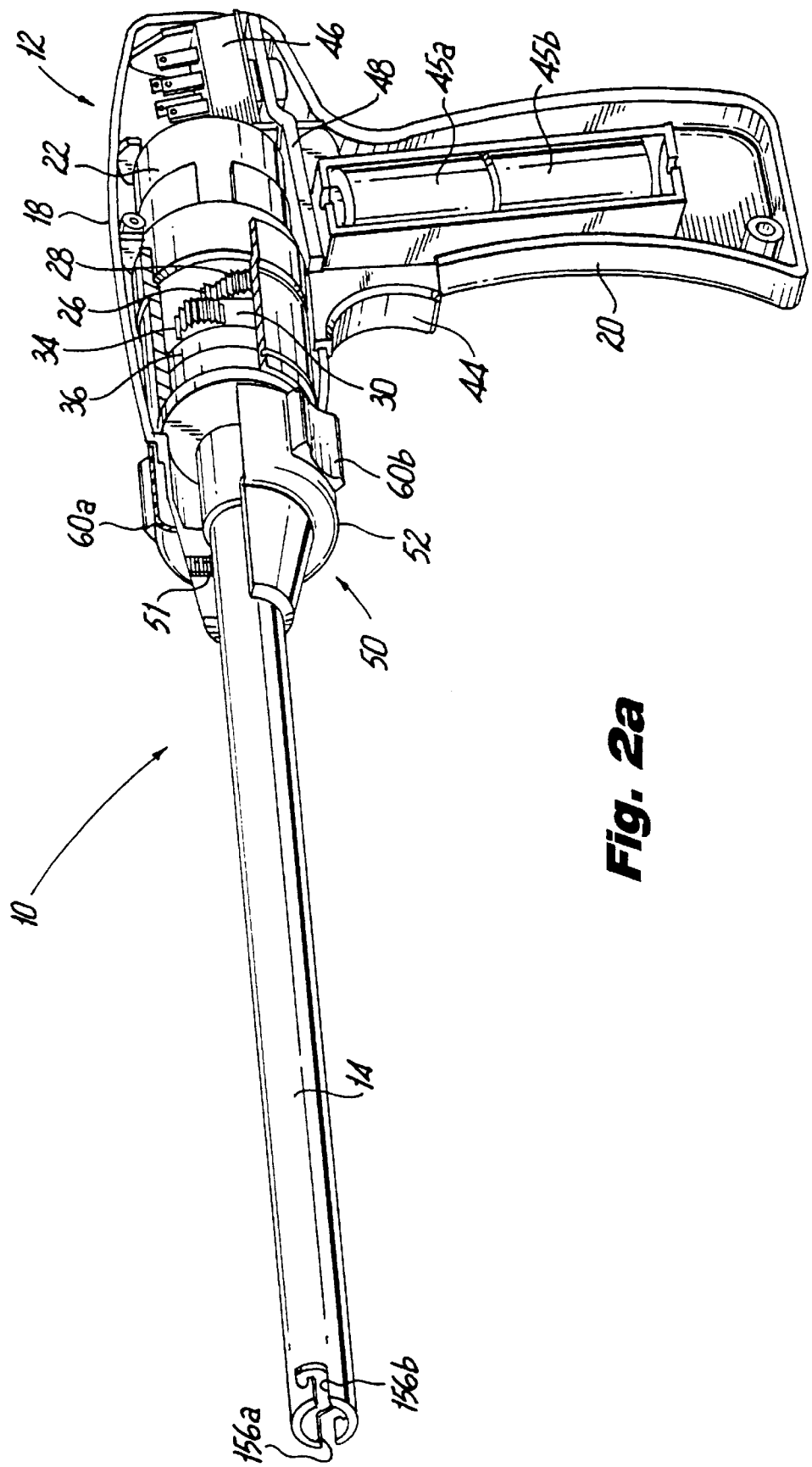
FIG. 2a is a perspective view of the elongated body portion and the handle assembly with one of the housing halves removed to illustrate the motor assembly.

Referring to FIGS. 2 and 2a, the handle portion 12 of surgical apparatus 10, composed of two housing halves, includes an elongated barrel section 18 and a handle gripping section 20. A motor assembly 22 having an output shaft (not shown) is disposed within the barrel section 18 and includes a gear set 24 for reducing the rotational speed of the output shaft and increasing the torque delivered by the motor assembly. Gear set 24 includes a pinion gear 26 which is directly driven by the output shaft of motor assembly 22. Pinion gear 26 drives a first set of planetary gears 28 which are supported on a carrier 30. The pinion portion of carrier 30 then drives the second set of planetary gears 34 which in turn drives the hub member 36. The ring gear 32 remains stationary, acting as a reaction point for planetary gears 28 and 34. A reception port 38 is formed in hub member 36 for receiving the proximal end 40 of an elongated drive shaft 42. Drive shaft 42 extends from hub 36 through the elongate body portion 14 of surgical apparatus 10 to the cartridge assembly 16. A shaft coupling is provided at the distal end of drive shaft 42 for detachably connecting the cartridge assembly 16 to the drive shaft 42. This arrangement will be discussed in greater detail below with respect to FIG. 6.

With continued reference to FIGS. 2 and 2a, motor assembly 22 is energized by a pair of power cells 45a and 45b which are disposed within the handle gripping section 20 of handle portion 12. As shown, handle portion 12 extends substantially perpendicular to the barrel portion 18. The power cells 45a, 45b can be lithium, alkaline, or nickel cadmium type bathes. A trigger 44 projects from gripping section 20 for controlling the operation of motor assembly 22. Preferably, trigger 44 is connected to a switching assembly 46 by a link bar 48. The switching assembly is preferably a double-pole-double-throw (DPDT) switch and is electrically connected to motor assembly 22. Preferably, the switch includes a first position corresponding to the output shaft of the motor assembly rotating in a first direction, a second position corresponding to the output shaft rotating in a second direction, and a third position wherein the motor assembly is not in operation. DPDT switching assemblies of this type are well known to the those skilled in the art.

Figure 2B:
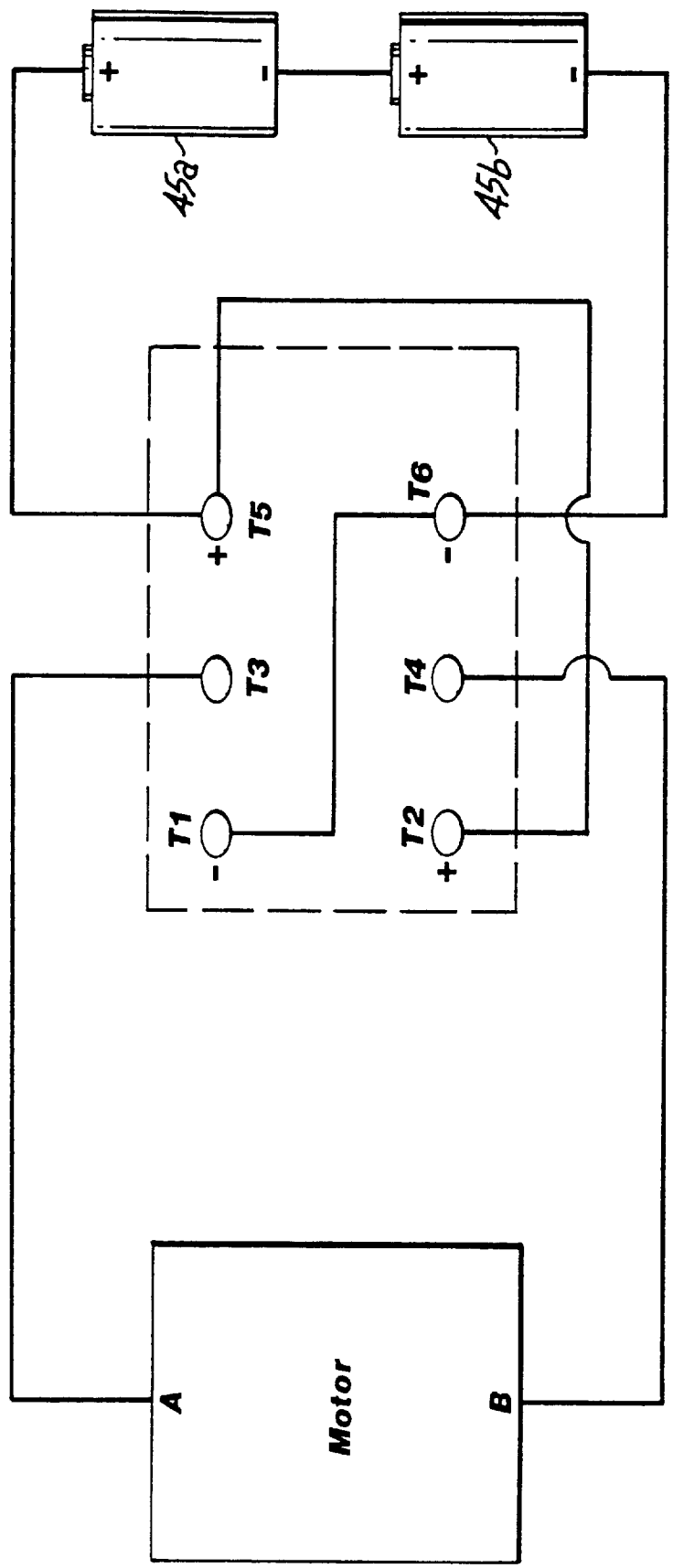
FIG. 2b is a schematic representation of the switching mechanism for selectively controlling the operation of the surgical apparatus.

FIG. 2b is a schematic representation of the switching mechanism. As shown, terminal T3 is wired to terminal A of the motor and terminal T4 is wired to terminal B of the motor. The positive terminal of the power cell 45a is connected to positive terminal T5 and the negative terminal of the power cell 45b is connected to negative terminal T6. When link bar 48 is moved proximally upon squeezing trigger 44, the two middle terminals T3, T4 connect to the respective rear terminals T5, T6. Thus, terminal A of the motor will be connected to the positive terminal of the switch and terminal B of the motor will be connected to the negative terminal of the switch, thereby rotating the motor shaft in a first direction to drive shaft 42 in a first direction to fire the fasteners. If it is desired at any time to stop firing, the trigger 44 is released to disconnect terminals T3, T4 from T5, T6. If it is desired to unclamp the tissue after the firing stroke has begun, trigger 44 is pulled distally so that the middle terminals T3 and T4 connect to front terminals T1, T2. Thus, terminal A of the motor will be connected to the negative terminal of the switch and terminal B will be connected to the positive terminal of the switch thereby reversing the direction of the motor and drive shaft.

Figure 4:
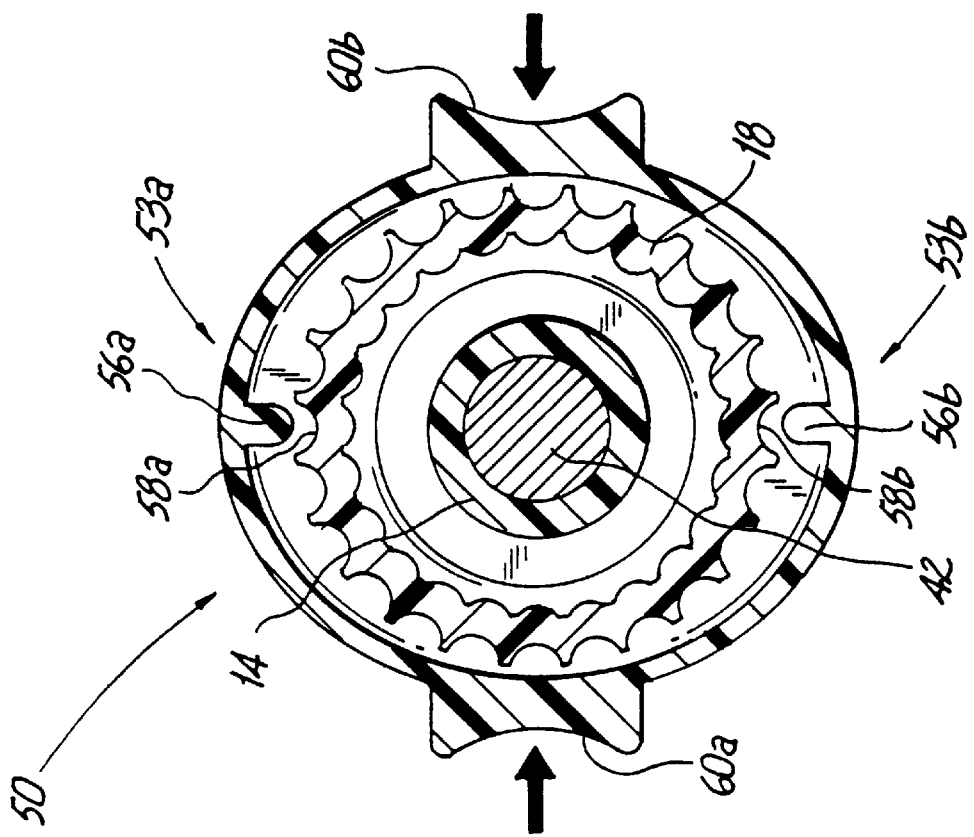
FIG. 4 is a cross-sectional view taken along line 3—3 of FIG. 2 with the rotation collar disengaged from the handle assembly to allow rotation of the elongated body portion.
Figure 3:
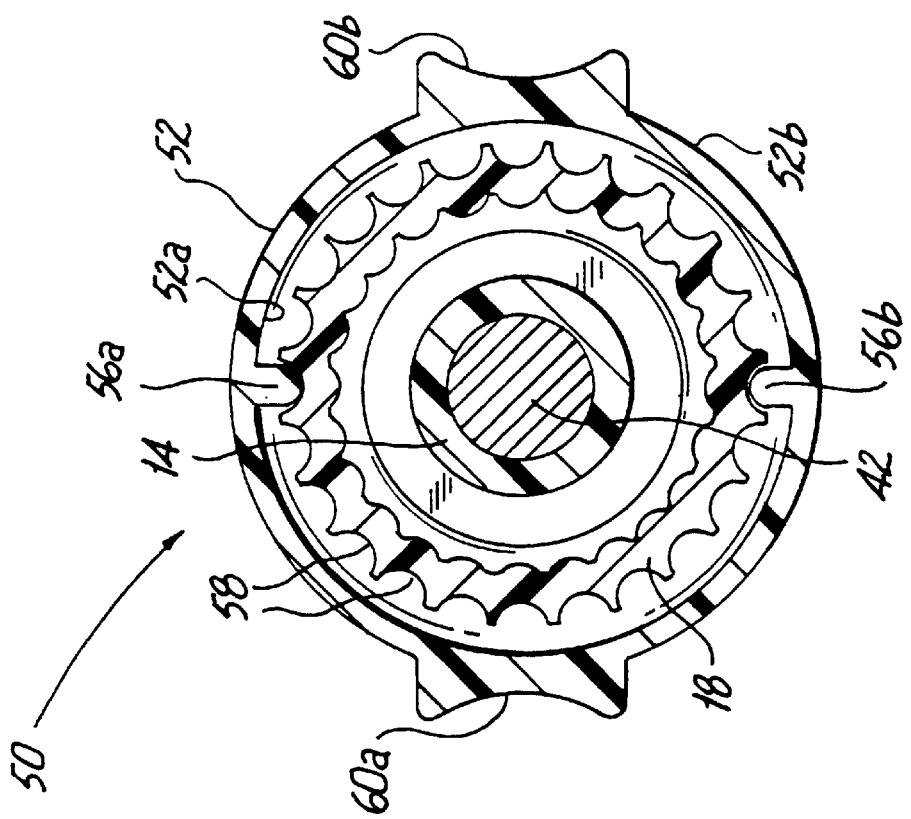
FIG. 3 is a cross-sectional view taken along line 3—3 of FIG. 2 with the rotation collar engaged with the barrel portion of the handle assembly.

Referring to FIGS. 3 and 4 in conjunction with FIGS. 2 and 2*a*, powered surgical apparatus 10 includes a rotator mechanism 50 for enabling axial rotation of the body portion 14 relative to the handle portion 12 to increase the operative range of the instrument Rotator mechanism 50 includes an annular collar 52 formed of a resilient material and connected to the proximal end of body portion 14 by a threaded fastener 51. A pair of diametrically opposed protuberances 56*a* and 56*b* extend radially inwardly from the inner surface 52*a* of collar 52 for selectively engaging a plurality of correspondingly configured recesses 58 defined about the circumference of the distal end portion of barrel section 18. When the protuberances 56*a*, 56*b* engage recesses 58 of barrel portion 58, collar 52 is locked in position and body portion 14 cannot rotate. Thus the body portion 14 will remain fixed as the drive shaft 42 extending therethrough rotates during a fastener applying operation.

A pair of diametrically opposed disengagement pads 60*a* and 60*b* are provided on an outer surface 52*b* of collar 52, 90° out of phase from the protuberances to release the protuberances to allow rotation of collar 52. Thus to axially rotate body portion 14 relative to handle portion 12, a radially inwardly directed force is applied to pads 60*a* and 60*b*, as illustrated in FIG. 4, causing portions 53*a*, 53*b* of the resilient collar 52 to flex radially outwardly. This flexure disengages protuberances 56*a* and 56*b* from corresponding recesses 58*a* and 58*b*. This frees collar 52 for rotation, thereby allowing body portion 14 to be rotated relative to the handle portion 12 to orient cartridge assembly 16 to a desired position.

Turning now to cartridge assembly 16, and referring to FIG. 5, cartridge assembly 16 is configured as a separate unit which is detachably connected to the distal end of elongated body portion 14. This enables the apparatus to be reloaded with a fresh cartridge for additional application of rows of fasteners. The detachability feature also enables the instrument to be manufactured as a semi-reusable instrument, if desired, wherein the handle portion 12 and elongate body portion 14 are resterilized and the cartridge assembly discarded after use. It is also contemplated that the entire apparatus could be disposable.

Cartridge assembly 16 includes two main structural portions, a cartridge adaptor 70 and an elongated housing channel 80. They are mounted to one another by a threaded fastener 75.

Adapter 70 includes a mounting portion 72 at its proximal end dimensioned for reception within the distal end of elongated body portion 14. An axial bore 74 extends through mounting portion 72 for rotatably supporting a cylindrical cartridge coupling 76. Cartridge coupling 76 is configured to connect at its distal end to the proximal end of an axial drive screw 78. Coupling 76 is detachably connected at its proximal end to a shaft coupling 140 which is connected to the distal end of drive shaft 42. This coupling which transmits rotational motion from the drive shaft 42 to the drive screw 78 will be discussed in greater detail below.

Housing channel 80 includes opposed side walls 80*a* and 80*b*, and a floor 80*c*. An aperture 82 is defined in floor 80*c* adjacent the proximal end of channel 80 for receiving fastener 75. Opposed apertures 83*a* and 83*b* are defined in the side walls 80*a* and 80*b* of housing channel 80 for receiving a pair of outwardly extending flanges 84*a* and 84*b* which are formed adjacent the proximal end of anvil member 86 and about which anvil member 86 pivots between closed and open positions to capture and release body tissue. A pair of spring members 85*a* and 85*b* are disposed within apertures 83*a* and 83*b* for biasing anvil 86 into an open position. Opposed engagement notches 88*a* and 88*b* are also defined in side walls 80*a* and 80*b*, adjacent the distal end of housing channel 80, for receiving a pair of detents on retaining cartridge 90, one of which is shown and designated by reference numeral 89. The detents are formed monolithically with the fastener retaining cartridge 90 and secure the cartridge within a distal portion of the housing channel 80.

With continuing reference to FIG. 5, cartridge assembly 16 includes an elongate actuation beam 100 for progressively moving anvil member 86 from an open position to a closed position with respect to retainer cartridge 90, and for concomitantly effecting the sequential ejection of a plurality of surgical fasteners from retainer cartridge 90. Actuation beam 100 is driven by the axial drive screw 78 which, as noted above, is driven by drive shaft 42. An actuation sled 120 is configured to translate through fastener retainer cartridge 90 to effectuate the ejection of surgical fasteners therefrom. Actuation sled 120 includes a base portion 122, a plurality of spaced apart upstanding cam plates 124, and a central drive plate 125. Each cam plate 124 has an angled cam surface for sequentially engaging a plurality of staple drivers (not shown) which drive surgical fasteners from retainer cartridge 90 through body tissue and into engagement with anvil depressions formed in anvil member 86. The leading edge 100*a* of actuation beam 100 engages drive plate 125 to drive actuation sled 120 through retainer cartridge 90. A cutting blade 130 is mounted on actuation beam 100 adjacent leading edge 100*a* and is configured to translate through cartridge assembly 16, trailing behind sled 120, to form an incision in stapled body tissue.

A stationary support mount 92 is disposed within cartridge assembly 16 to both guide the longitudinal translation of actuation beam 100, and support the distal end 78*a* of axial drive screw 78. The proximal end 78*b* of drive screw 78 engages coupling 76 which, as noted above, is connected to drive shaft 42 via coupling 140. A follower nut 94 is thredably associated with drive screw 78 and is mounted within a follower housing 95.

Follower housing 95 is mounted in such a manner so as to translate in a longitudinal direction in response to axial rotation of drive screw 78. Proximal elongate beam extensions 96 and 98 of actuation beam 100 operatively connect actuation beam 100 to follower housing 95 so that the actuation beam 100 translates distally with the follower housing.

A distal end of actuation beam 100 includes a retention flange 102 for supporting a generally cylindrical cam roller 104 and an engagement slot 106 for retaining a substantially planar cam beam 108. Cam roller 104 engages and translates relative to an upper clamming surface 110 of anvil member 86 to effect the progressive closure thereof as follower housing 95 and actuation beam 100 translate through housing channel 80 to fire the fasteners. Cam beam 108 engages and translates relative to the outer surface of the floor 80c of housing channel 80 to balance the forces exerted upon anvil member 86 by cam roller 104 during closure. A longitudinal slot 112 is defined in the floor 80c of housing channel 80 and a corresponding longitudinal slot 114 is defined in anvil member 86 to accommodate the longitudinal translation of actuation beam 100. A transverse slot 114a is defined at the distal end of anvil slot 114 to receive cam roller 104 at the end of its translation, and thereby permit anvil member 86 to return to an open position under the bias of spring 85a and 85b following a fastening operation. Thus, the body tissue is automatically unclamped as soon as all the fasteners have been fired.

Figure 8:
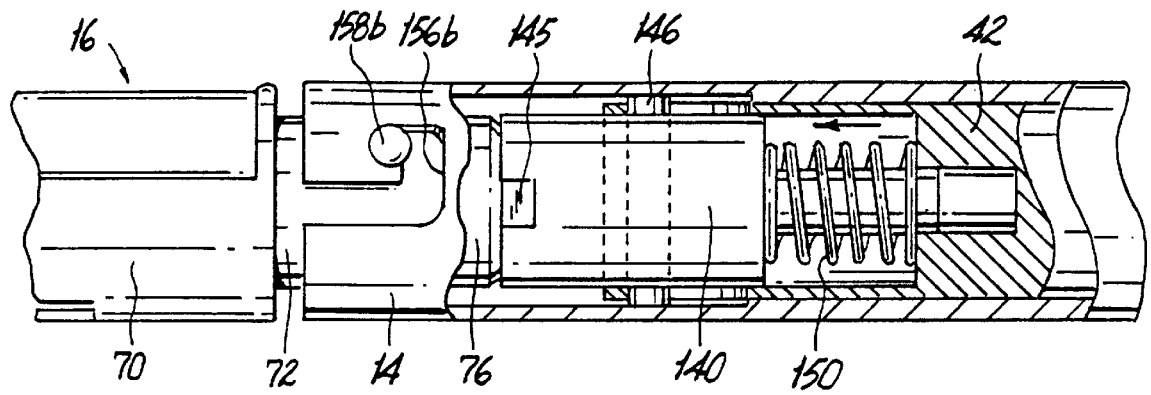
FIGS. 7 and 8 are side elevational views in partial cross-section of a distal end portion of the instrument body illustrating the connection of the carridge assembly of FIG. 5 to the elongated body portion.
Figure 7:
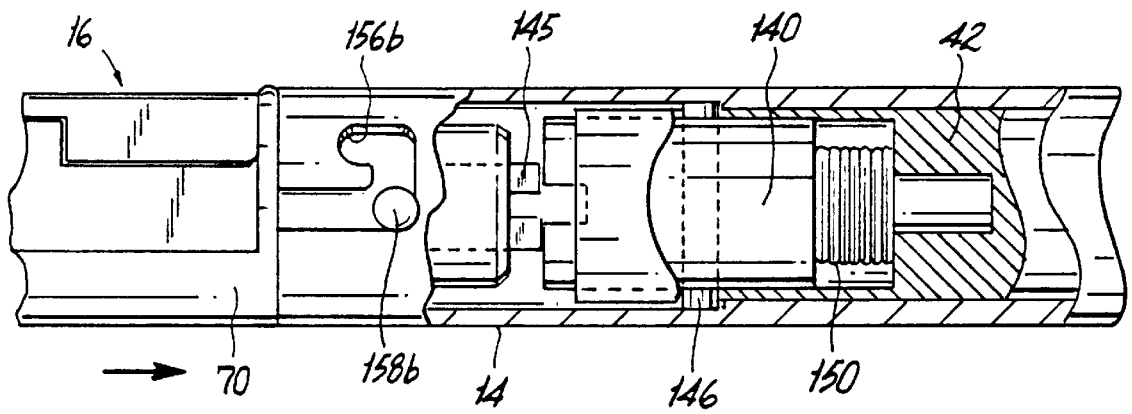
Figure 6:
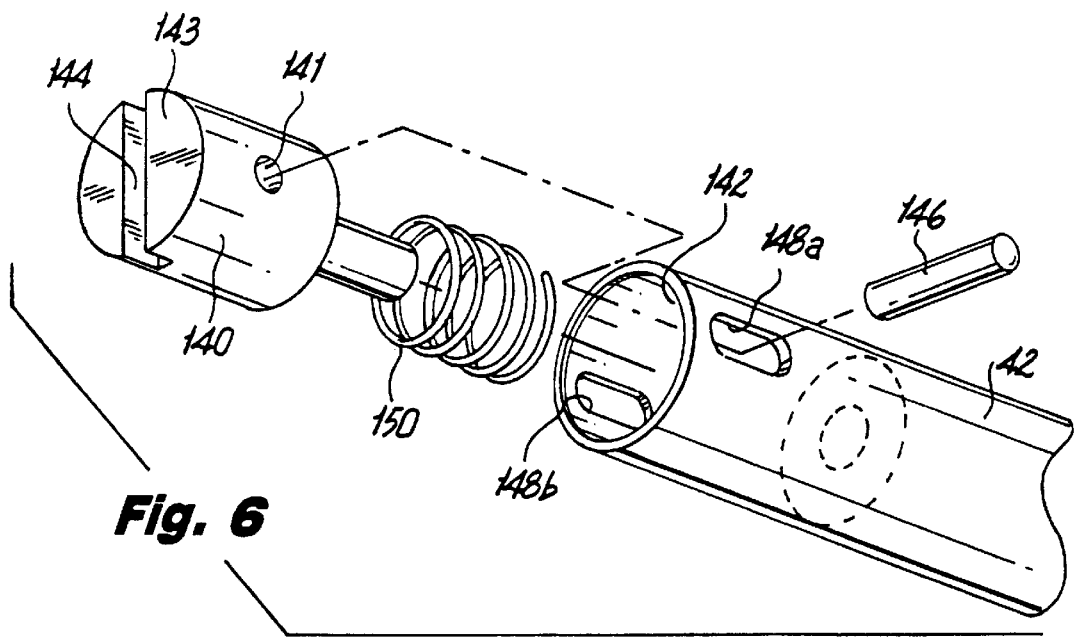
FIG. 6 is a perspective view of a distal end portion of the drive shaft of the powered surgical apparatus of FIG. 1 illustrating the coupling arrangement for detachably connecting the cartridge assembly of FIG. 5 to the drive shaft.

Referring now to FIGS. 6–9, as noted hereinabove, the cartridge assembly 16 of surgical apparatus 10 is configured as a separate unit which is detachably mounted to the distal end of body portion 14 via a bayonet coupling. In addition, as noted above, axial drive screw 78 is detachably connected to drive shaft 42 through cartridge coupling 76 and shaft coupling 140. As best seen in FIG. 6, shaft coupling 140 is slidably supported in a cavity 142 formed in the distal end of drive shaft 42. A transverse slot 144 is formed in the distal end of coupling 140 for engaging a corresponding teeth 145 extending from the proximal end of cartridge coupling 76 (see also FIG. 5). A pin 146, which is supported in opposed shaft slots 148a and 148b and extends through openings 141 in shaft coupling 140, maintains shaft coupling 140 in cavity 142 and permits the longitudinal translation of shaft coupling 140 against the bias of a coupling spring 150. The function of coupling spring 150 is two-fold. Firstly, if slot 144 of coupling 140 and teeth 145 of coupling 76 are not aligned when cartridge assembly 16 is inserted into the distal end of body portion 14, coupling spring 150 will compensate for the misalignment and facilitate engagement of the couplings upon initial rotation of drive shaft 42. This occurs by initial compression of the spring 150 as teeth 145 abut surface 143 of coupling 140. When drive shaft 42 initially rotates and slot 144 becomes aligned with teeth 145, the spring 150 forces coupling 140 distally so slot 144 engages teeth 145. The second function of coupling spring 150, as best seen in FIGS. 7 and 8, is to bias cartridge adaptor 70 in a distal direction when the bayonet coupling which maintains cartridge assembly 16 in body portion 14 is engaged. The bayonet coupling includes a generally J-shaped engagement slot 156 formed in body portion 14 and corresponding engagement pins 158a and 158b which extend radially outwardly from cartridge adaptor 70 (see also FIG. 5). During attachment of the cartridge assembly 16, the proximal end of cartridge adaptor 70 is axially inserted into the distal end of body portion 14 (compressing spring 150) and is rotated approximately 20° to engage pins 158a and 158b in corresponding slots 156a and 156b (see FIG. 1). At such a time, coupling spring 150 urges shaft coupling 140 and adaptor 70 distally to maintain pins 158a and 158b in an engaged position within slots 156a and 156b.

Figure 11:
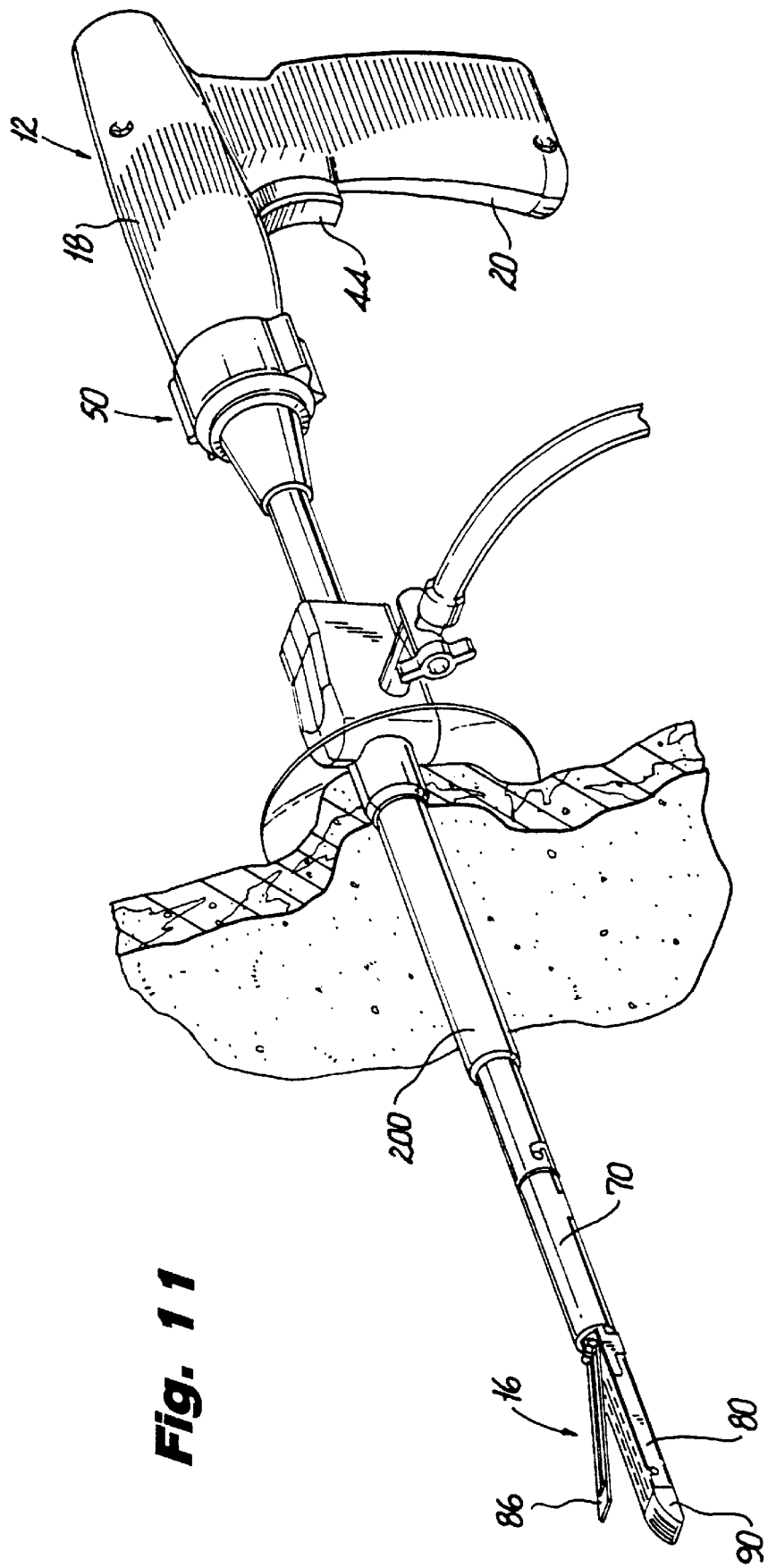
FIG. 11 is a perspective view of the powered surgical stapling apparatus of FIG. 1 inserted through a trocar cannula.

Referring to FIGS. 9–11, in operation, the apparatus is inserted through a trocar cannula 200 to access the surgical site. When body tissue is captured between anvil member 86 and retainer cartridge 90, trigger 44 is depressed to actuate motor assembly 22, and thereby cause gear set 24 to transfer rotational motion to drive shaft 42, which, in turn, transfers rotational motion to axial drive screw 78 through couplings 76 and 140. At such a time, follower housing 95 translates in a longitudinal direction, driving actuation beam 100 distally. As actuation beam 100 translates distally, cam roller 104 progressively moves anvil member 86 from the normally biased open position shown in FIG. 9, to the closed clamped position illustrated in FIG. 10. Concomitantly, actuation sled 120 is driven from the proximal position illustrated in FIG. 9, through retention cartridge 90, to the distal-most position shown in FIG. 10, sequentially driving surgical fasteners through body tissue 160. When cam roller 104 reaches the distal end of longitudinal slot 114, it drops into transverse slot 114a, permitting anvil 86 to return to an open position and release the stapled body tissue 160. At the conclusion of the fastener applying operation, cartridge assembly 16 is manipulated in such a manner so as to disengage pins 158a and 158b from slots 156a and 156b, and detach carridge adaptor 70 from body portion 14. Thereafter, a new cartridge assembly containing a plurality of surgical fasteners and a staple firing sled disposed in a proximal position may be mounted to the apparatus in the same manner as described above for another stapling procedure.

Although the subject apparatus has been described with respect to preferred embodiments, it will be readily apparent to those having ordinary skill in the art to which it appertains that changes and modifications may be made thereto without departing from the spirit or scope of the appended claims.

What is claimed is:

1. A self-contained powered surgical apparatus for applying surgical fasteners to body tissue comprising:
 a) a handle assembly;
 b) a motor assembly disposed within the handle assembly;
 c) a power source disposed within the handle assembly for energizing the motor assembly;
 d) an elongated body extending distally from the handle assembly;
 e) a cartridge assembly detachably connected to a distal end portion of the elongated body and including:
  i) a housing supporting a plurality of surgical fasteners;
  ii) an anvil associated with the housing and mounted for movement between an open position and a closed position;
  iii) an actuation mechanism configured to translate relative to the housing and the anvil to progressively move the anvil from the open position to the closed position and to sequentially eject surgical fasteners from the housing to be formed against the anvil;
  iv) an axial drive screw threadably associated with the actuation mechanism for effectuating the translation thereof; and
 f) an elongated drive shaft extending through the elongated body and detachably coupling the axial drive screw of the cartridge assembly to the motor assembly.

2. A powered surgical apparatus as recited in claim 1, wherein the handle assembly includes an elongate barrel portion within which the motor assembly is disposed, and a depending handle gripping portion within which the power source is disposed.

3. A powered surgical apparatus as recited in claim 1, further comprising a trigger mechanism associated with the handle assembly for selectively actuating the motor assembly.

4. A powered surgical apparatus as recited in claim 3, further comprising a switching mechanism associated with the trigger mechanism for selectively reversing the polarity of the motor assembly.

5. A powered surgical apparatus as recited in claim 4, wherein the elongated body and cartridge assembly are rotatable with respect to the handle assembly.

6. A powered surgical apparatus as recited in claim 1, further comprising means for preventing rotation of the elongated body and the cartridge assembly.

7. A powered surgical apparatus as recited in claim 5, wherein the preventing means comprises a plurality of indentations circumferentially disposed about a distal portion of the handle assembly, and an annular collar formed of a resilient material and mounted about a proximal end portion of the elongated body, the annular collar including a pair of diametrically opposed radially inwardly extending protuberances dimensioned to normally engage the indentations formed on the handle assembly, and which are disengaged from the indentations by applying a radially inwardly directed force on the collar.

8. A powered surgical apparatus as recited in claim 1, wherein the cartridge assembly is detachably mounted to the elongated body by a bayonet-type coupling arrangement.

9. A powered surgical apparatus as recited in claim 8, wherein the bayonet-type coupling includes an engagement slot defined in a distal end portion of the elongated body and a corresponding engagement pin associated with a proximal end portion of the cartridge assembly.

10. A powered surgical apparatus as recited in claim 1, wherein a distal end of the elongated drive shaft is releasably coupled to a proximal end of the axial drive screw by a spring biased coupling mechanism.

11. A powered surgical apparatus as recited in claim 10, wherein the coupling mechanism includes a compression spring, the spring facilitating axial alignment of the proximal end of the axial drive screw and the distal end of the elongated drive shaft.

12. A power surgical apparatus as recited in claim 10, further comprising a shaft coupling interconnecting the elongated drive shaft and the axial drive screw, the shaft coupling being rotatably fixed but longitudinally slidable with respect to the drive shaft and being longitudinally biased into operable engagement with the axial drive screw, and a cartridge coupling operably connected to the axial drive screw, the cartridge coupling having proximally extending teeth and the shaft coupling having distally extending teeth, the shaft coupling teeth being biased into engagement with the cartridge coupling teeth.

13. A cartridge assembly for a surgical apparatus configured to sequentially apply a plurality of surgical fasteners to body tissue, the apparatus including an elongated body and an actuator mounted for axial rotation within the elongated body, the cartridge assembly comprising:
   a) a housing supporting a plurality of surgical fasteners and configured to be detachably mounted to a distal end portion of the elongated body of the apparatus;
   b) an anvil associated with the housing and mounted for movement with respect thereto between an open position and a closed position;
   c) an actuation assembly configured to translate relative to the housing and the anvil to progressively move the anvil from the open position to the closed position and to concomitantly sequentially eject surgical fasteners from the housing to be formed against the anvil; and
   d) an axial drive screw thredably associated with the actuation assembly for effectuating the translation thereof, a proximal end of the drive screw being configured to detachably couple with a distal end of the actuator, whereby axial rotation of the actuator causes longitudinal translation of the actuation assembly.

14. A cartridge assembly as recited in claim 13, further comprising a cutting blade configured to translate through the cartridge assembly in conjunction with the actuation assembly to form an incision in stapled body tissue.

15. A cartridge assembly as recited in claim 14, wherein the anvil is normally biased into the open position.

16. A cartridge assembly as recited in claim 15, wherein the anvil includes a fastener forming surface against which fasteners are driven when ejected from the housing, and an opposed outer camming surface.

17. A cartridge assembly as recited in claim 16, wherein the actuation assembly includes a cylindrical roller cam dimensioned and configured to engage the outer camming surface of the anvil to effect the progressive closure thereof during the longitudinal translation of the actuation assembly.

18. A cartridge assembly as recited in claim 17, wherein a slot is defined in the anvil to receive the cam roller and permit the anvil to return to a normally biased open position at the conclusion of a fastening operation.

19. A surgical apparatus comprising:
   a) a handle assembly;
   b) an elongated body extending distally from the handle assembly; and
   c) a cartridge assembly detachably connected to the elongated body by a bayonet-type coupling, the cartridge assembly comprising:
      i) a housing supporting a plurality of surgical fasteners;
      ii) an anvil movable with respect to the housing between open and closed positions;
      iii) an actuation mechanism configured to translate relative to the housing and anvil to move the anvil from the open to the closed position and to eject the surgical fasteners from the housing to be formed against the anvil; and
      iv) a drive member operably associated with the handle assembly to effect translation of the actuation mechanism.

20. A surgical apparatus as recited in claim 19, wherein the drive member is an axial drive screw.

21. A surgical apparatus as recited in claim 20, further including a motor disposed within the handle assembly and an elongated drive shaft extending through the elongated body, the elongated drive shaft coupling the axial drive screw of the cartridge assembly to the motor assembly.

22. A surgical apparatus as recited in claim 21, further comprising a trigger mechanism associated with the handle assembly for selectively actuating the motor assembly.

23. A surgical apparatus as recited in claim 21, further comprising a shaft coupling interconnecting the elongated drive shaft and the axial drive screw, the shaft coupling being rotatably fixed but longitudinally slidable with respect to the drive shaft and being longitudinally biased into operable engagement with the axial drive screw, and a cartridge coupling operably connected to the axial drive screw, the cartridge coupling having proximally extending teeth and the shaft coupling having distally extending teeth, the shaft coupling teeth being biased into engagement with the cartridge coupling teeth.

24. A surgical apparatus as recited in claim 21, wherein the handle assembly includes an elongate barrel portion within which the motor assembly is disposed, and a depending handle gripping portion within which a power source is disposed.

25. A surgical apparatus as recited in claim 21, further comprising a switching mechanism associated with a trigger mechanism for selectively reversing the polarity of the motor assembly, and wherein the cartridge is detachably mounted to the elongated body by a bayonet-type coupling arrangement.

26. A surgical apparatus as recited in claim 19, further including a motor assembly and a power source disposed within the handle assembly.

* * * * *